US 12,121,639 B2

(12) United States Patent
Ohta et al.

(10) Patent No.: US 12,121,639 B2
(45) Date of Patent: Oct. 22, 2024

(54) BLOOD PURIFICATION APPARATUS AND METHOD OF VERIFYING MEDICAL COMPONENT BY BLOOD PURIFICATION APPARATUS

(71) Applicant: Nikkiso Company Limited, Tokyo (JP)

(72) Inventors: Masaaki Ohta, Shizuoka (JP); Kazuhide Ono, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 902 days.

(21) Appl. No.: 17/080,036

(22) Filed: Oct. 26, 2020

(65) Prior Publication Data
US 2021/0038796 A1 Feb. 11, 2021

Related U.S. Application Data

(63) Continuation of application No. PCT/JP2019/018518, filed on May 9, 2019.

(30) Foreign Application Priority Data

May 10, 2018 (JP) .................................. 2018-091451

(51) Int. Cl.
*A61M 1/14* (2006.01)
*A61M 1/36* (2006.01)
*G16H 20/40* (2018.01)

(52) U.S. Cl.
CPC ............ *A61M 1/14* (2013.01); *A61M 1/3621* (2013.01); *G16H 20/40* (2018.01); *A61M 2205/6072* (2013.01); *A61M 2205/6081* (2013.01)

(58) Field of Classification Search
CPC .................. A61M 1/14; A61M 1/3621; A61M 2205/6072; A61M 2205/6081;
(Continued)

(56) References Cited

U.S. PATENT DOCUMENTS

| 2004/0154966 A1 | 8/2004 | Meziere et al. |
| 2010/0094194 A1 | 4/2010 | Peters et al. |
| 2010/0282834 A1* | 11/2010 | Devergne ................ A61M 1/16 715/744 |

(Continued)

FOREIGN PATENT DOCUMENTS

| JP | H11-128342 A | 5/1999 |
| JP | 2003-033371 A | 2/2003 |

(Continued)

OTHER PUBLICATIONS

English language machine translation of RU2574367, 86 pages, No Date.*

(Continued)

*Primary Examiner* — Pranav N Patel
(74) *Attorney, Agent, or Firm* — Young Basile Hanlon & MacFarlane, P.C.

(57) ABSTRACT

A blood purification apparatus including an apparatus body to which a medical component for giving blood purification treatment to a patient is to be attached; a storage unit that stores treatment information regarding the blood purification treatment for the patient; a reading unit capable of reading component information of the medical component held by an information-holding unit; and a verifying unit capable of comparing the component information read by the reading unit and the treatment information stored in the storage unit and verifying whether or not the medical component is appropriate for being attached to the apparatus body. The medical component is sealed in a sterile bag before being attached to the apparatus body. Furthermore, the reading unit is capable of reading the component information in the information-holding unit from an outside of the sterile bag.

9 Claims, 5 Drawing Sheets

(58) Field of Classification Search
CPC ...... A61M 2205/60; A61M 2205/6009; A61M 2205/12; A61M 2205/3592; A61M 2205/6018; A61M 2205/6063; G16H 20/40; G16H 40/60; G16H 20/17
See application file for complete search history.

(56) References Cited

U.S. PATENT DOCUMENTS

| | | | |
|---|---|---|---|
| 2010/0315231 A1 | 12/2010 | Rada | |
| 2016/0101278 A1* | 4/2016 | Norris | A61M 1/154 604/29 |
| 2018/0073989 A1* | 3/2018 | Lura | G01N 21/77 |
| 2018/0110911 A1* | 4/2018 | Kogoshi | A61M 1/3643 |

FOREIGN PATENT DOCUMENTS

| | | | | |
|---|---|---|---|---|
| JP | 2008000318 A | 1/2008 | | |
| JP | 2008-220774 A | 9/2008 | | |
| JP | 2009131595 A | 6/2009 | | |
| JP | 3199614 U | 9/2015 | | |
| JP | 2015-213642 A | 12/2015 | | |
| RU | 2574367 C2 * | 2/2016 | ............. | A61M 1/14 |
| WO | 2004/069312 A1 | 8/2004 | | |
| WO | 2006/037429 A1 | 4/2006 | | |
| WO | 2008/129344 A1 | 10/2008 | | |
| WO | WO-2014105755 A1 * | 7/2014 | .......... | A61M 1/1039 |
| WO | WO-2016208706 A1 * | 12/2016 | .......... | A61M 1/1006 |
| WO | 2017/035420 A1 | 3/2017 | | |

OTHER PUBLICATIONS

Extended European Search Report for Application No. 19799267.0, dated Feb. 1, 2022.
Japanese Office Action for Application No. 2018-091451, dated Mar. 28, 2022.
Potentially Related U.S. Appl. No. 15/343,652, filed Nov. 4, 2016.

* cited by examiner

BLOOD PURIFICATION APPARATUS AND METHOD OF VERIFYING MEDICAL COMPONENT BY BLOOD PURIFICATION APPARATUS

CROSS-REFERENCE TO RELATED APPLICATION(S)

This application is a continuation of International Application No. PCT/JP2019/018518, filed on May 9, 2019, which claims priority to Japanese Application No. 2018-091451, filed on May 10, 2018, the entire disclosures of which are hereby incorporated by reference.

FIELD

The present teachings relate to a blood purification apparatus to which a medical component is attached for giving blood purification treatment, and a method of verifying a medical component by a blood purification apparatus.

BACKGROUND

In general, blood purification treatment such as hemodialysis treatment is given in a treatment room of a hospital where a plurality of blood purification apparatuses are installed, and a plurality of patients (for example, 10 to 50 patients) are to be treated sequentially or substantially simultaneously. In a preparation performed before the blood purification treatment, medical components such as a blood circuit and a dialyzer are attached to each apparatus body. Using the thus attached medical components, blood purification treatment is performed. Such medical components are disposable components that are to be disposed of after every treatment and are typically sealed in sterile bags.

As disclosed by PTL 1 for example, a known blood purification apparatus is configured to verify (compare) whether or not a medical component attached to an apparatus body is appropriate for conditions of the treatment that is about to be performed. Thus, the performance of treatment with any inappropriate medical component attached to the apparatus body can be prevented, and the safety in the blood purification treatment can be increased.

PTL 1: International Publication No. 2008/129344 the teachings of which are expressly incorporated by reference herein for all purposes.

SUMMARY

In the above known technique, however, the verification of whether or not the medical component is appropriate is made after the medical component is attached to the apparatus body. Therefore, if a medical component is verified to be inappropriate for the conditions of the treatment, the medical component has to be disposed of, which imposes a burden on the medical institution. Specifically, before the treatment, a medical component is taken out of a sterile bag by opening the bag and is then attached to an apparatus body. Therefore, if the medical component is verified to be inappropriate for the conditions of the treatment, it is difficult to keep the medical component sterile until the next treatment. Hence, the medical component has to be disposed of.

The present teachings may have been conceived in view of the above circumstances and provides a blood purification apparatus capable of verifying a medical component with a sterile bag unopened, and a method of verifying a medical component by a blood purification apparatus.

Variation 1 may provide a blood purification apparatus including an apparatus body to which a medical component for giving blood purification treatment to a patient is to be attached; a storage unit that stores treatment information regarding the blood purification treatment for the patient; a reading unit capable of reading component information of the medical component held by an information-holding unit; and a verifying unit capable of comparing the component information read by the reading unit and the treatment information stored in the storage unit and verifying whether or not the medical component is appropriate for being attached to the apparatus body. The medical component is sealed in a sterile bag before being attached to the apparatus body. Furthermore, the reading unit is capable of reading the component information in the information-holding unit from an outside of the sterile bag.

Variation 2 according to variation 1, in the blood purification apparatus according to variation 1, the information-holding unit is provided on the sterile bag.

Variation 3 may comprise the blood purification apparatus according to variation 1 or 2, the apparatus body has an attaching position to which the medical component is attachable. Furthermore, the reading unit is capable of reading the component information in the information-holding unit when the information-holding unit is at a position different from the attaching position.

Variation 4 may comprise the blood purification apparatus according to any of variations 1 to 3, the information-holding unit is a bar code, a two-dimensional code, a data matrix code, a color label, or an identification mark.

Variation 5 may comprise the blood purification apparatus according to any of variations 1 to 3, the information-holding unit is a transmitting unit capable of transmitting the component information to the reading unit.

Variation 6 may comprise the blood purification apparatus according to any of variations 1 to 5, the reading unit is capable of reading the component information in the information-holding unit when the information-holding unit is at a work position where the sterile bag is opened and the medical component is taken out of the sterile bag.

Variation 7 may comprise the blood purification apparatus according to any of variations 1 to 6, the information-holding unit is pasted on an outer surface or an inner surface of the sterile bag or on the medical component packed in the sterile bag.

Variation 8 may comprise the blood purification apparatus according to any of variations 1 to 7, a plurality of medical components are packed in the sterile bag. Furthermore, the verifying unit is capable of collectively comparing pieces of component information regarding the plurality of medical components and collectively verifying whether or not the medical components are appropriate for being attached to the apparatus body.

Variation 9 may comprise a method of verifying a medical component by a blood purification apparatus, the apparatus including an apparatus body to which a medical component for giving blood purification treatment to a patient is to be attached; a storage unit that stores treatment information regarding the blood purification treatment for the patient; a reading unit capable of reading component information of the medical component held by an information-holding unit; and a verifying unit capable of comparing the component information read by the reading unit and the treatment information stored in the storage unit and verifying whether or not the medical component is appropriate for being attached to the apparatus body. The medical component is sealed in a sterile bag before being attached to the apparatus body. Furthermore, the component information in the information-holding unit is read by the reading unit from an outside of the sterile bag.

Variation 10 may comprise the method of verifying a medical component by a blood purification apparatus according to variation 9, the information-holding unit is provided on the sterile bag.

Variation 11 may comprise the method of verifying a medical component by a blood purification apparatus according to variation 9 or 10, the apparatus body has an attaching position to which the medical component is attachable. Furthermore, the component information in the information-holding unit is read by the reading unit when the information-holding unit is at a position different from the attaching position.

Variation 12 may comprise the method of verifying a medical component by a blood purification apparatus according to variations 9 to 11, the information-holding unit is a bar code, a two-dimensional code, a data matrix code, a color label, or an identification mark.

Variation 13 may comprise the method of verifying a medical component by a blood purification apparatus according to any of variations 9 to 11, the information-holding unit is a transmitting unit capable of transmitting the component information to the reading unit.

Variation 14 may comprise the method of verifying a medical component by a blood purification apparatus according to any of variations 9 to 13, the component information in the information-holding unit is read by the reading unit when the information-holding unit is at a work position where the sterile bag is opened and the medical component is taken out of the sterile bag.

Variation 15 may comprise the method of verifying a medical component by a blood purification apparatus according to any of variations 9 to 14, the information-holding unit is pasted on an outer surface or an inner surface of the sterile bag or on the medical component packed in the sterile bag.

Variation 16 may comprise the method of verifying a medical component by a blood purification apparatus according to any of variations 9 to 15, a plurality of medical components are packed in the sterile bag. Furthermore, the verifying unit collectively compares pieces of component information regarding the plurality of medical components and collectively verifies whether or not the medical components are appropriate for being attached to the apparatus body.

Variation 17 according to the variation of each of variations 1 and 9, the medical component is sealed in the sterile bag before being attached to the apparatus body. Furthermore, the reading unit reads the component information in the information-holding unit from the outside of the sterile bag. Therefore, the verification of the medical component can be performed with the sterile bag unopened.

Variation 18 according to the variation of each of variations 2 and 10, the information-holding unit is provided on the sterile bag. Therefore, the verification of the medical component can be performed by reading the component information in the information-holding unit provided on the sterile bag, with the sterile bag unopened.

Variation 19 according to the variation of each of variations 3 and 11, the apparatus body has the attaching position to which the medical component is attachable. Furthermore, the reading unit reads the component information in the information-holding unit when the information-holding unit is at a position different from the attaching position. Therefore, the component information held by the information-holding unit can be easily read before the medical component is attached to the apparatus body.

Variation 20 according to the variation of each of variations 4 and 12, the information-holding unit is a bar code, a two-dimensional code, a data matrix code, a color label, or an identification mark. That is, a general-purpose element can be employed as the information-holding unit that holds the component information. Therefore, the increase in the manufacturing cost can be suppressed.

Variation 21 according to the variation of each of variations 5 and 13, the information-holding unit is a transmitting unit capable of transmitting the component information to the reading unit. Therefore, the information-holding unit can hold a relatively large amount of component information.

Variation 22 according to the variation of each of variations 6 and 14, the reading unit reads the component information in the information-holding unit when the information-holding unit is at the work position where the sterile bag is opened and the medical component is taken out of the sterile bag. Therefore, the reading of the component information in the information-holding unit, the opening of the sterile bag, and the attaching of the medical component can be performed smoothly. Thus, the work efficiency can be increased.

Variation 23 according to the variations of each of variations 7 and 15, the information-holding unit is pasted on the outer surface or the inner surface of the sterile bag or on the medical component packed in the sterile bag. Therefore, the reading unit can easily and assuredly read the component information from the outside of the sterile bag that is unopened.

Variation 24 according to the variation of each of variations 8 and 16, a plurality of medical components are packed in the sterile bag. Furthermore, the verifying unit collectively compares pieces of component information regarding the plurality of medical components and collectively verifies whether or not the medical components are appropriate for being attached to the apparatus body. Therefore, work time can be made shorter than in a case where medical components are verified one by one.

DETAILED DESCRIPTION

Embodiments and variations of the present teachings will now be described specifically with reference to the drawings.

Figure 1:
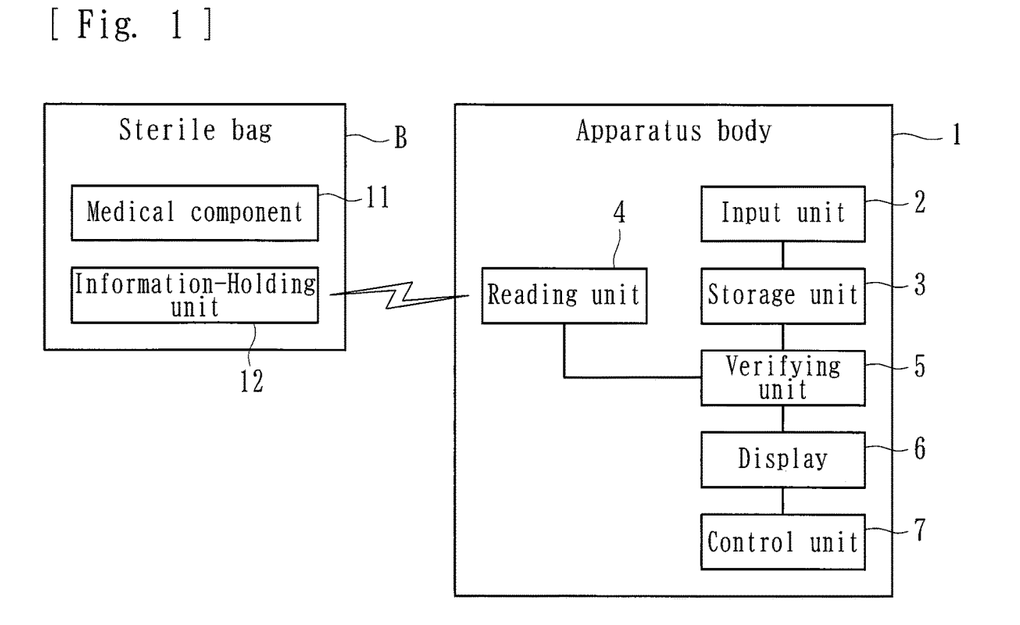
FIG. 1 is a block diagram of a blood purification apparatus according to an embodiment of the present invention.
Figure 2:
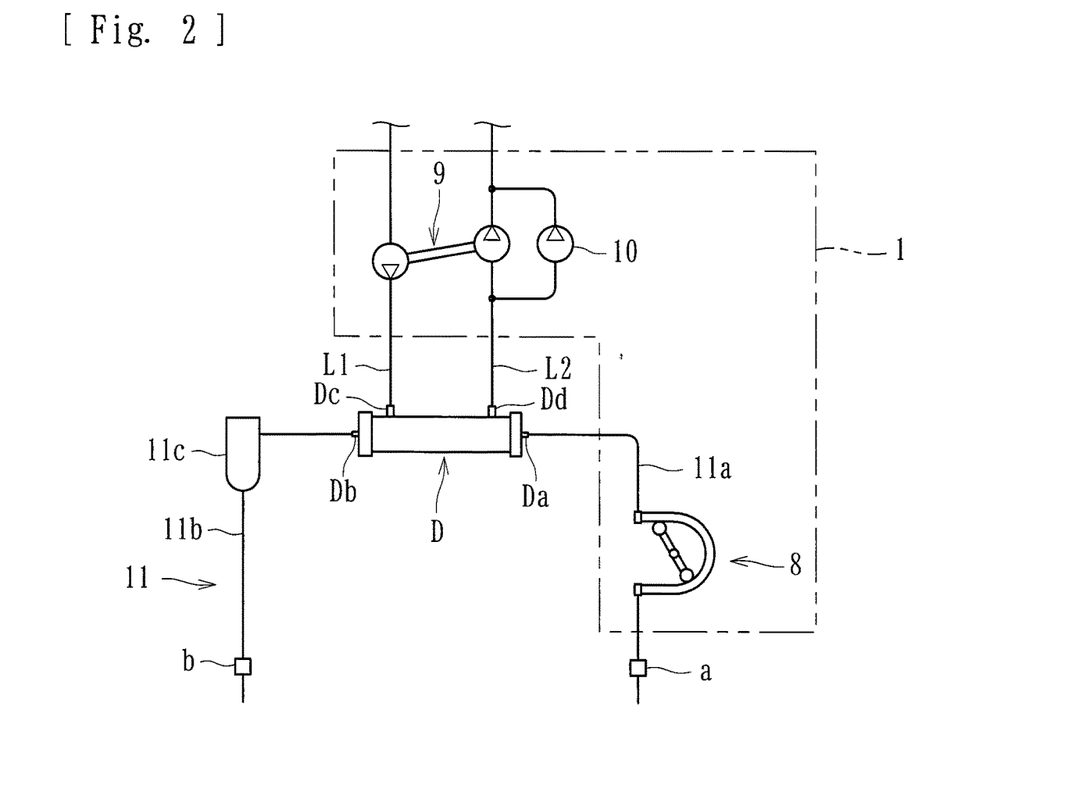
FIG. 2 is a schematic diagram of a blood circuit as a medical component included in the blood purification apparatus.
Figure 3:
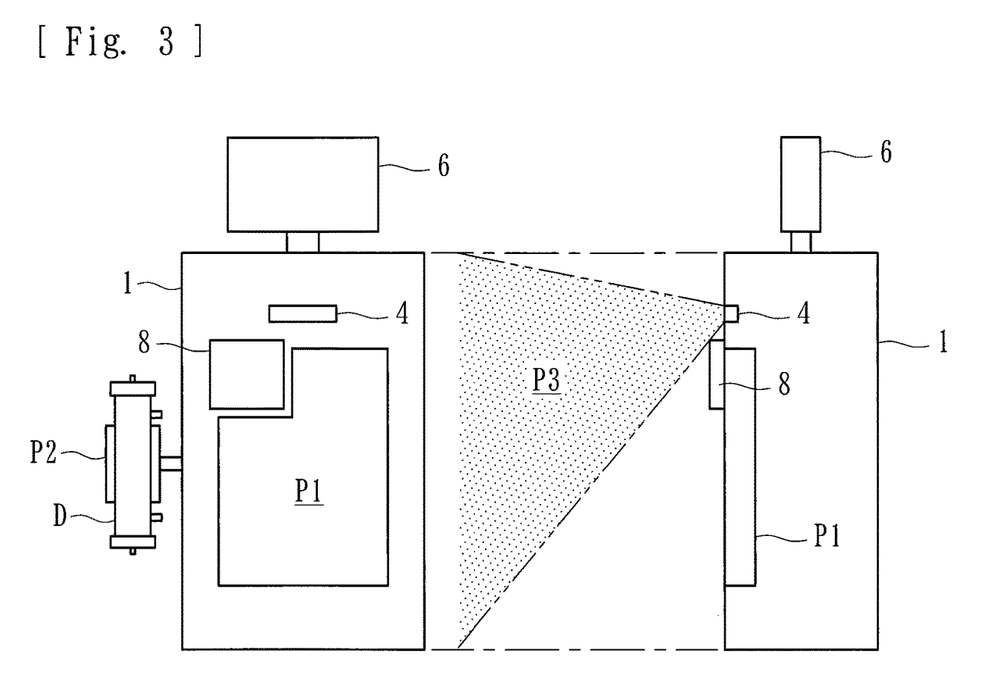
FIG. 3 is a schematic diagram of an apparatus body and a reading unit included in the blood purification apparatus.

A blood purification apparatus according to the present embodiment is a dialysis apparatus for giving hemodialysis treatment and includes, as illustrated in FIGS. 1 to 3, an apparatus body 1 in which an input unit 2, a storage unit 3, a reading unit 4, a verifying unit 5, a display 6, and a control unit 7 are provided; and a medical component 11 to be attached to the apparatus body 1.

The medical component 11 is to be attached to the apparatus body 1 so that blood purification treatment is given to a patient. The medical component 11 is a disposable component to be disposed of after every treatment. Before the medical component 11 is attached to the apparatus body 1, the medical component 11 is sealed in a sterile bag B. The medical component 11 can be taken out by opening the sterile bag B. The sterile bag B is sterilized in any of various ways such as steam sterilization, gamma-ray sterilization, EOG (ethylene oxide gas) sterilization, and electron-beam sterilization.

The medical component 11 according to the present embodiment is a blood circuit through which blood of a patient is caused to extracorporeally circulate during the blood purification treatment. As illustrated in FIG. 2, the blood circuit basically includes an arterial blood circuit 11a and a venous blood circuit 11b each made of a flexible tube. A dialyzer D as a blood purifier is connected to the arterial blood circuit 11a and to the venous blood circuit 11b.

The arterial blood circuit 11a is provided at a distal end thereof with a connector (a) for connection of an arterial puncture needle thereto. The arterial blood circuit 11a is further provided at a halfway position thereof with a peristaltic blood pump 8. The venous blood circuit 11b is provided at a distal end thereof with a connector (b) for connection of a venous puncture needle thereto. The venous blood circuit 11b is further provided at a halfway position thereof with an air-trap chamber 11c. The blood pump 8 is provided on the apparatus body 1. The blood circuit is attached to the apparatus body 1 such that part of the arterial blood circuit 11a is set in the blood pump 8.

When the blood pump 8 is activated while a patient is punctured with the arterial puncture needle and the venous puncture needle, the patient's blood flows through the arterial blood circuit 11a and reaches the dialyzer D, where the blood is purified. Then, the blood flows through the venous blood circuit 11b while undergoing bubble removal in the air-trap chamber 11c and returns into the patient's body. Thus, the patient's blood is purified with the dialyzer D while extracorporeally circulating through the blood circuit. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The dialyzer D has, in a housing thereof, a blood introduction port Da, a blood delivery port Db, a dialysate introduction port Dc, and a dialysate delivery port Dd. The blood introduction port Da is connected to a proximal end of the arterial blood circuit 11a. The blood delivery port Db is connected to a proximal end of the venous blood circuit 11b. The dialysate introduction port Dc and the dialysate delivery port Dd are connected to a dialysate introduction line L1 and a dialysate drain line L2, respectively, extending from the apparatus body 1.

The dialyzer D houses a plurality of hollow fibers. Spaces inside the respective hollow fibers form flow routes for blood (blood flow routes), and spaces between the inner peripheral surface of a housing and the outer peripheral surfaces of the hollow fibers form flow routes for dialysate (dialysate flow routes). The hollow fibers each have a number of microscopic holes (pores), thereby forming a hollow fiber membrane (blood purification membrane). Impurities and the like contained in the blood flowing in the blood flow routes are allowed to permeate through the hollow fiber membranes into the dialysate flowing in the dialysate flow routes and to be discharged.

A duplex pump 9 is provided on the apparatus body 1 and over the dialysate introduction line L1 and the dialysate drain line L2. A flow route that bypasses the duplex pump 9 is provided with an ultrafiltration pump 10 for removing water from the patient's blood flowing in the dialyzer D. One end of the dialysate introduction line L1 is connected to the dialyzer D (the dialysate introduction port Dc), and the other end is connected to a dialysate supply device (not illustrated) that prepares a dialysate at a predetermined concentration. One end of the dialysate drain line L2 is connected to the dialyzer D (the dialysate delivery port Dd), and the other end is connected to a drainage unit, not illustrated. The dialysate supplied from the dialysate supply device flows through the dialysate introduction line L1 into the dialysate flow routes in the dialyzer D, and further flows through the dialysate drain line L2 into the drainage unit.

The sterile bag B according to the present embodiment is provided with an information-holding unit 12 that holds component information regarding the medical component 11. Specifically, the information-holding unit 12 is a bar code, a two-dimensional code (a QR code (a registered trademark)), a data matrix code, a color label, or an identification mark. The component information regarding the medical component 11 that is held by the information-holding unit 12 includes, in the case of the blood circuit for example, product code, expiration date, lot number, and so forth.

The information-holding unit 12 according to the present invention is provided by printing or the like on a sheet or the like pasted on the outer surface of the sterile bag B. When the information-holding unit 12 is placed over the reading unit 4, the component information held by the information-holding unit 12 can be read in a noncontact manner. The information-holding unit 12 is not limited to a bar code, a two-dimensional code (a QR code (a registered trademark)), a data matrix code, a color label, or an identification mark and may be a transmitting unit (an RF tag or the like) capable of transmitting component information to the reading unit 4 over radio waves or the like.

The information-holding unit 12 only needs to be provided on the sterile bag B such that the component information is readable by the reading unit 4 from the outside of the sterile bag B. For example, the information-holding unit 12 may be a bar code, a two-dimensional code, a data matrix code, a color label, or an identification mark that is directly printed on the sterile bag B or may be provided on the inner surface of the sterile bag B. Moreover, the information-holding unit 12 may be pasted on the medical component 11 packed in the sterile bag B.

If the information-holding unit 12 is provided on the inner surface of the sterile bag B or on the medical component 11 and is a bar code, a two-dimensional code, a data matrix code, a color label, or an identification mark, the sterile bag B is preferably made of a transparent or translucent material so that the information-holding unit 12 can be read therethrough. If the information-holding unit 12 is a transmitting unit (an RF tag or the like) capable of transmitting component information to the reading unit 4 over radio waves or the like, the sterile bag B may not necessarily be made of a transparent or translucent material.

The apparatus body 1 forms a housing of the blood purification apparatus and is provided with the blood pump 8 as illustrated in FIG. 3. The apparatus body 1 has an attaching position P1 to which the blood circuit (a medical component) is to be attached, an attaching position P2 to which the dialyzer D is to be attached, and the display 6 such as a touch panel. The apparatus body 1 is installed near a bed on which a patient is to sit or lie. Blood purification treatment is performed in a state where the patient is punctured with the arterial puncture needle and the venous puncture needle of the blood circuit attached to the attaching position P1.

The apparatus body 1 provided with the blood pump 8, the duplex pump 9, and the ultrafiltration pump 10 is further provided with various devices, such as actuators and electromagnetic valves, for performing blood purification treatment. Such components are controlled by the control unit 7, whereby the blood purification treatment is performed. Furthermore, the apparatus body 1 according to the present embodiment includes the input unit 2, the storage unit 3, the reading unit 4, the verifying unit 5, the display 6, and the control unit 7.

The input unit 2 allows a doctor, a medical worker, or the like to input predetermined information to the apparatus body 1 through an operation performed on, for example, a touch panel of the display 6, separate operation buttons, or the like. Specifically, treatment information regarding the blood purification treatment for the patient is inputted through the input unit 2. Examples of the treatment information include treatment mode (the type of treatment), priming volume (priming volume varying among adult, child, and infant), and so forth.

The storage unit 3 is a storage medium connected to the input unit 2 and is capable of storing the treatment information regarding the blood purification treatment for the patient that is inputted through the input unit 2. Specifically, the storage unit 3 stores the treatment information, such as treatment mode (the type of treatment) and priming volume (priming volume varying among adult, child, and infant), inputted through the input unit 2 for the blood purification treatment to be performed, so that the treatment information can be compared with the component information read by the reading unit 4.

The reading unit 4 is capable of reading the component information held by the information-holding unit 12 and is, for example, a bar-code reader or the like capable of applying predetermined light to a bar code or the like and reading the component information from the light thus reflected. Since the reading unit 4 can read the component information from the outside of the sterile bag B, the comparison and verification by the verifying unit 5 can be performed before the sterile bag B is opened. Specifically, when a worker holding an unopened sterile bag B places the information-holding unit 12 over (near) the reading unit 4, the reading unit 4 can read the component information in the information-holding unit 12 in a noncontact manner. The reading unit 4 may be a unit capable of reading the component information when the information-holding unit 12 is brought into contact with the reading unit 4.

The reading unit 4 according to the present embodiment is also capable of reading the component information in the information-holding unit 12 when the information-holding unit 12 is at a position (a work position P3) different from the attaching position P1 defined on the apparatus body 1. Specifically, as illustrated in FIG. 3, a predetermined area on the front side (in front) of the apparatus body 1 is defined as the work position P3, where the work of opening the sterile bag and taking out the medical component can be performed. The worker brings up an unopened sterile bag B to the work position P3 such that the information-holding unit 12 is located at the work position P3 (to be positioned within the area defined as the work position P3), whereby the reading unit 4 can read the component information held by the information-holding unit 12. The reading unit 4 may be provided at a position different from the position on the front side (the front face) of the apparatus body 1 (for example, on a side or rear face of the apparatus body 1, on the front face of the display 6 and on the frame around the screen thereof, on a side or rear face of the display 6, or the like).

The verifying unit 5 is capable of comparing the component information read by the reading unit 4 and the treatment information stored in the storage unit 3 and verifying whether or not the medical component of interest is appropriate for being attached to the apparatus body 1. For example, if the storage unit 3 has treatment information regarding a treatment to be performed in a predetermined treatment mode, whether or not the medical component (blood circuit) of interest is appropriate for that treatment mode is verified. If the storage unit 3 has treatment information regarding a treatment intended for children or infants, whether or not the medical component (blood circuit) of interest is appropriate for the priming volume that is set for the treatment intended for children or infants is verified.

Then, if the component information read by the reading unit 4 and compared with the treatment information stored in the storage unit 3 matches the treatment information (regarding the treatment conditions, the component to be used, and so forth), the medical component of interest is verified to be appropriate for being attached to the apparatus body 1. Accordingly, the result (a message telling that the medical component is appropriate) is displayed on, for example, the display 6. If the component information read by the reading unit 4 and compared with the treatment information stored in the storage unit 3 does not match the treatment information (regarding the treatment conditions, the component to be used, and so forth), the medical component of interest is verified to be inappropriate for being attached to the apparatus body 1. Accordingly, the result (a message telling that the medical component is inappropriate) is displayed on, for example, the display 6.

In such a manner, the verifying unit 5 can inform the medical worker of whether or not the medical component of interest is appropriate for being attached to the apparatus body 1. Therefore, if a medical component is verified to be appropriate by the verifying unit 5, the sterile bag B is opened and the medical component is taken out and is attached to the position P1 of the apparatus body 1. Thus, the blood purification treatment can be started. On the other hand, if a medical component is verified to be inappropriate by the verifying unit 5, the medical component can be replaced with an appropriate one with the sterile bag B unopened.

Figure 4:
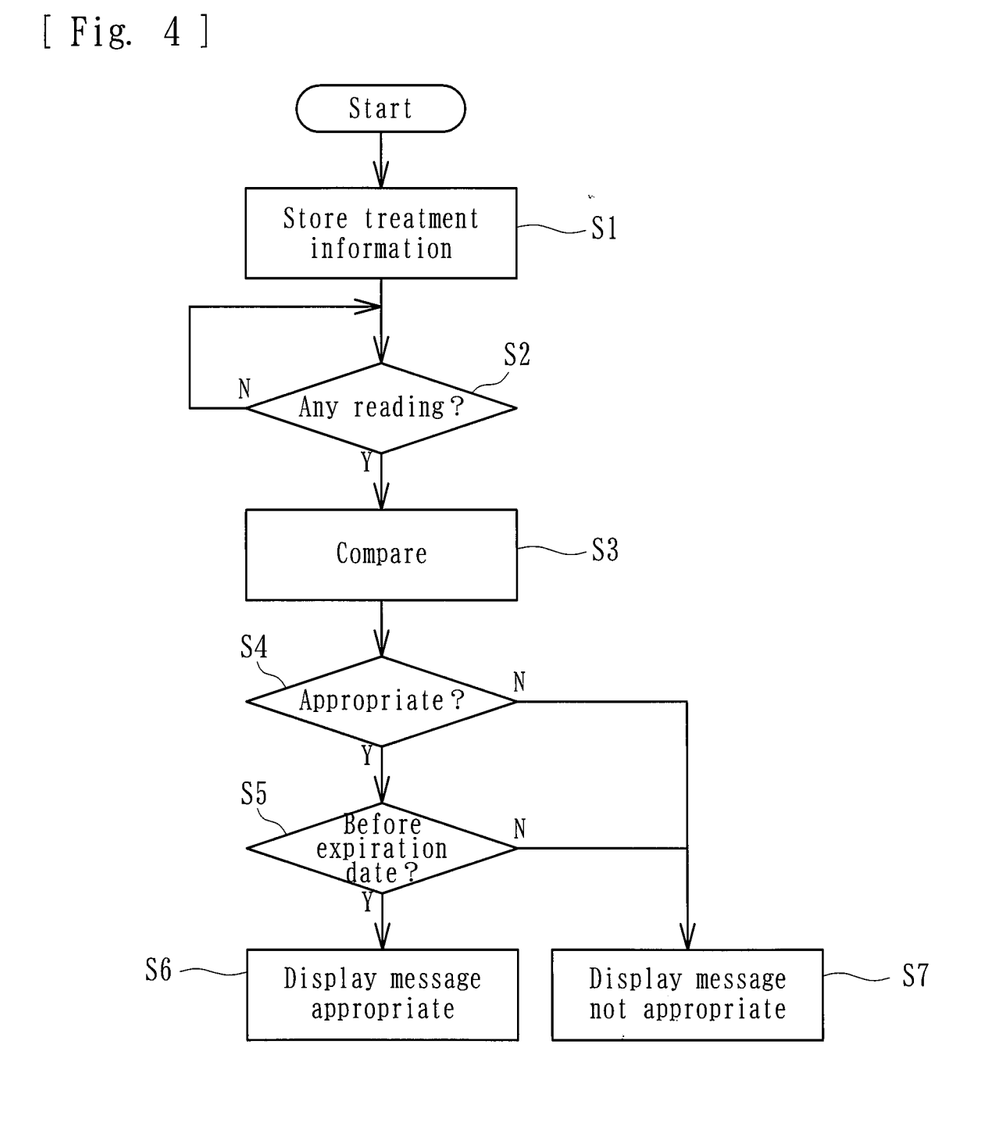
FIG. 4 is a flow chart of a control process executed by the blood purification apparatus.

Now, a control process according to the present embodiment will be described with reference to a flow chart illustrated in FIG. 4.

First, treatment information inputted through the input unit 2 is stored in the storage unit 3 (S1). Subsequently, whether or not any component information has been read by the reading unit 4 is checked (S2). If it is determined in S2 that some component information has been read, the process proceeds to S3, where the component information read by the reading unit 4 and the treatment information stored in the storage unit 3 are compared (checked for any differences).

Subsequently, in accordance with the comparison in S3, whether or not the medical component of interest is appropriate for being attached to the apparatus body 1 is verified (S4). If the medical component of interest is verified to be appropriate for being attached to the apparatus body 1, whether or not a predetermined expiration date is yet to be reached is checked in S5. If it is determined in S5 that the expiration date is yet to be reached, the process proceeds to S6, where a message telling that the medical component is appropriate for being attached to the apparatus body 1 and the expiration date is yet to be reached is displayed on the screen of the display 6.

On the other hand, if it is verified in S4 that the medical component is inappropriate for being attached to the apparatus body 1 or if it is determined in S5 that the expiration date has been reached, the process proceeds to S7, where a message telling that the medical component is inappropriate for being attached to the apparatus body 1 or the expiration date has been reached is displayed on the screen of the display 6. The message telling that the medical component has been verified to be inappropriate for being attached to the apparatus body 1 or the predetermined expiration date has been reached may be provided by another informing unit (such as an indicator lamp or a speaker) instead of or in combination with the display 6 (that is, the message may be provided by only another informing unit or by both the display 6 and another informing unit).

Moreover, the result of the verification may be displayed on the screen of the display 6 only if it is verified in S4 that the medical component is inappropriate for being attached to the apparatus body 1 or if it is determined in S5 that the expiration date has been reached. That is, the result of the verification may be undisplayed on the screen of the display 6 if it is verified in S4 that the medical component is appropriate for being attached to the apparatus body 1 or if it is determined in S5 that the expiration date is yet to be reached.

According to the present embodiment, the medical component is sealed in the sterile bag B before being attached to the apparatus body 1. Furthermore, the reading unit 4 reads the component information in the information-holding unit 12 from the outside of the sterile bag B. Therefore, the verification of the medical component 11 (the verification of whether or not the medical component is appropriate for being attached to the apparatus body 1) can be performed with the sterile bag B unopened. In particular, the information-holding unit 12 according to the present embodiment is provided on the sterile bag B. Therefore, the verification of the medical component can be performed by reading the component information in the information-holding unit 12 provided on the sterile bag B, with the sterile bag B unopened.

The apparatus body 1 according to the present embodiment has the attaching position P1 to which the medical component 11 is attachable. Furthermore, the reading unit 4 reads the component information in the information-holding unit 12 when the information-holding unit 12 is at a position different from the attaching position P1. Therefore, the component information held by the information-holding unit 12 can be easily read before the medical component 11 is attached to the apparatus body 1.

The information-holding unit 12 according to the present embodiment is a bar code, a two-dimensional code, a data matrix code, a color label, or an identification mark. That is, a general-purpose element can be employed as the information-holding unit 12 that holds the component information. Therefore, the increase in the manufacturing cost can be suppressed. Moreover, if the information-holding unit 12 is a transmitting unit capable of transmitting the component information to the reading unit 4, the information-holding unit 12 can hold a relatively large amount of component information.

The reading unit 4 reads the component information in the information-holding unit 12 when the information-holding unit 12 is at the work position P3 where the sterile bag B is opened and the medical component is taken out of the sterile bag B. Therefore, the reading of the component information in the information-holding unit 12, the opening of the sterile bag B, and the attaching of the medical component 11 can be performed smoothly. Thus, the work efficiency can be increased. The information-holding unit 12 according to the present embodiment is pasted on the outer surface or the inner surface of the sterile bag B or on the medical component 11 packed in the sterile bag B. Therefore, the reading unit 4 can easily and assuredly read the component information from the outside of the sterile bag B that is unopened.

Figure 5:
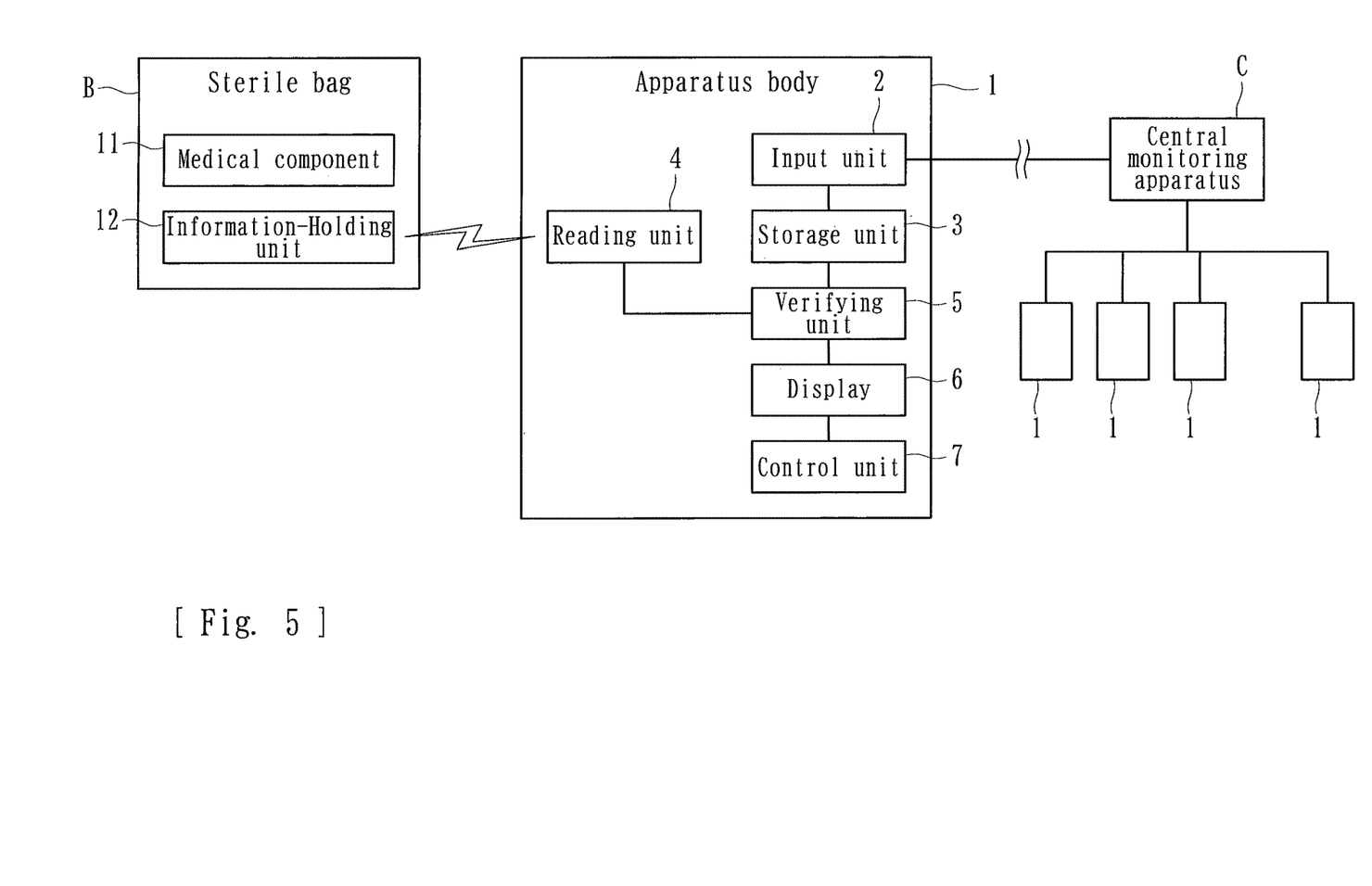
FIG. 5 is a schematic diagram illustrating another embodiment of the present invention (an embodiment in which blood purification apparatuses are connected to a central monitoring apparatus).

While the present embodiment has been described above, the present invention is not limited thereto. The medical component to be packed in the sterile bag B is not limited to the blood circuit (including the arterial blood circuit 11a and the venous blood circuit 11b) described in the present embodiment and may be any other medical component such as the dialyzer D, a continuous slow hemofiltration device, a hemoadsorption device, a plasma separation device, a plasma fractionation device, a plasma adsorption device, an anticoagulant, a physiological saline solution, a dialysis solution, a blood product, a catheter, or the like. For example, if the medical component is the dialyzer D, the component information to be held by the information-holding unit 12 may include the type of hollow fibers (blood purification membranes), filtration coefficient, product code, expiration date, lot number, and so forth. The present invention may also be applied to a system, illustrated in FIG. 5, including a central monitoring apparatus C electrically connected to input units 2 of a plurality of apparatus bodies 1 and being capable of transmitting pieces of treatment information regarding the blood purification treatment for respective patients to the respective apparatus bodies 1. In such a case, the pieces of treatment information to be inputted through the respective input units 2 and stored in the respective storage units 3 may be transmitted from the central monitoring apparatus C.

Figure 6:
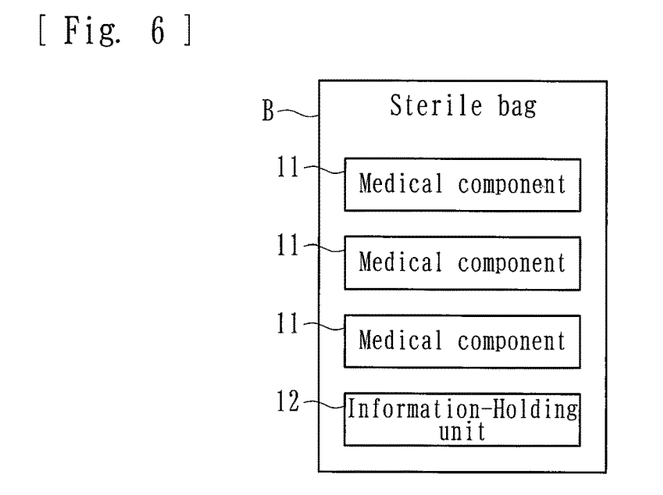
FIG. 6 is a schematic diagram illustrating yet another embodiment of the present invention (an embodiment in which a plurality of medical components are packed in a sterile bag).

Furthermore, as illustrated in FIG. 6, a plurality of medical components 11 (for example, a blood circuit, a dialyzer D, and so forth) may be packed in the sterile bag B, and the verifying unit 5 may be capable of collectively comparing pieces of component information regarding the plurality of medical components 11 and collectively verifying whether or not the medical components are appropriate for being attached to the apparatus body 1. In such a case, work time can be made shorter than in a case where medical components 11 are verified one by one.

Figure 7:
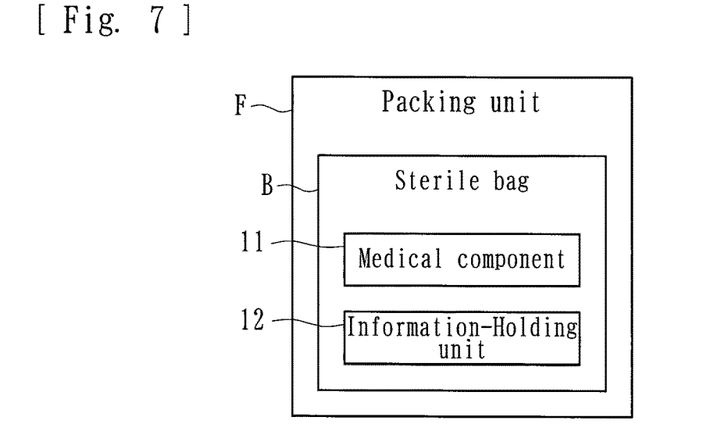
FIG. 7 is a schematic diagram illustrating yet another embodiment of the present invention (an embodiment in which a sterile bag is packed in a packing unit).
Figure 8:
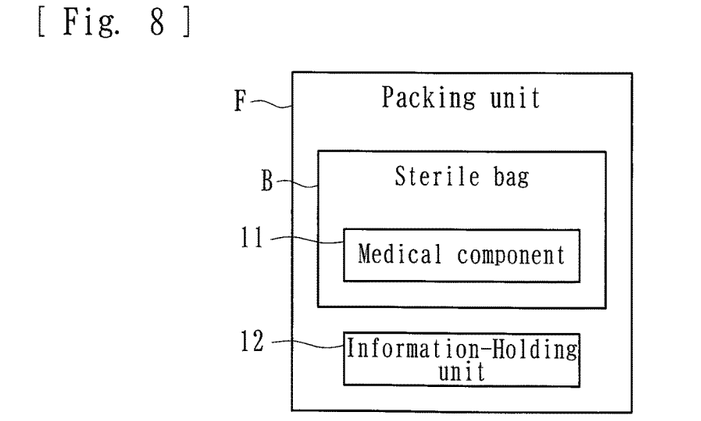
FIG. 8 is a schematic diagram illustrating yet another embodiment of the present invention (an embodiment in which a sterile bag is packed in a packing unit and an information-holding unit is provided inside or outside the packing unit and outside the sterile bag).

Furthermore, as illustrated in FIG. 7, a medical component 11 packed in a sterile bag B provided with an information-holding unit 12 may be packed in a separate packing unit F (including wrapping paper, a wrapping bag, a wrapping box, and the like). Moreover, the information-holding unit 12 may not necessarily be provided on the sterile bag B. For example, as illustrated in FIG. 8, the information-holding unit 12 may be provided on a separate packing unit F in which the sterile bag B is packed and at a position other than on the sterile bag B (including positions inside and outside the packing unit F). While the present embodiment concerns a dialysis apparatus intended for dialysis treatment, the present invention may be applied to any other apparatus capable of purifying blood of a patient (for example, a blood purification apparatus, a hemoadsorption apparatus, a plasma adsorption apparatus, or the like to be used in hemodiafiltration, hemofiltration, AFBF, continuous slow hemofiltration, hemoadsorption, selective cytapheresis, plasma exchange, double filtration plasmapheresis, or plasma adsorption).

The present invention is applicable to any blood purification apparatus having a different appearance, additional functions, and so forth and to any method of verifying a medical component by using a blood purification apparatus, as long as the medical component is sealed in a sterile bag before being attached to an apparatus body, and a reading unit reads component information in an information-holding unit from the outside of the sterile bag.

1 apparatus body
2 input unit
3 storage unit
4 reading unit
5 verifying unit
6 display
7 control unit
8 blood pump
9 duplex pump
10 ultrafiltration pump
11 medical component
11a arterial blood circuit
11b venous blood circuit
12 information-holding unit
D dialyzer (blood purifier)
B sterile bag

The invention claimed is:

1. A method of verifying a medical component, comprising an information-holding unit, with a blood purification apparatus, the blood purification apparatus comprising:
an apparatus body to which the medical component for giving blood purification treatment to a patient is to be attached, the apparatus body comprising:
an attaching position that the medical component is configured to be attached;
a storage unit;
a reading unit located on a front side of the apparatus body, and the reading unit is capable of applying a predetermined light to a predetermined area in the front side of the apparatus body; and
a verifying unit, wherein the method comprises:
storing treatment information, in the storage unit, regarding the blood purification treatment for the patient;
reading, with the reading unit the predetermined light reflected from the information-holding unit positioned in the predetermined area, component information of the medical component held by the information-holding unit; and
comparing, with the verifying unit, the component information read by the reading unit and the treatment information stored in the storage unit and verifying whether the medical component is appropriate for being attached to the apparatus body,
wherein the medical component is sealed in a sterile bag before being attached to the attaching position of the apparatus body,
wherein the component information in the information-holding unit is read by the reading unit from an outside of the sterile bag;
wherein the component information in the information-holding unit is read by the reading unit when the information-holding unit is at a position different from the attaching position;
wherein the medical component is a component that provides the blood purification treatment to the patient and includes a blood circuit with an air-trap chamber connected thereto and
wherein a priming volume of the component is compared to a treatment by the verification unit to determine if the component is appropriate for the priming volume that is set.

2. The method according to claim 1, wherein the information-holding unit is provided on the sterile bag.

3. The method according to claim 1, wherein the information-holding unit is a bar code, a two-dimensional code, a data matrix code, a color label, or an identification mark.

4. The method according to claim 1, further comprising:
transmitting the component information to the reading unit from a transmitting unit of the information holding unit.

5. The method according to claim 1, wherein the component information in the information-holding unit is read by the reading unit when the information-holding unit is at a work position where the sterile bag is opened and the medical component is taken out of the sterile bag.

6. The method according to claim 1, wherein the information-holding unit is pasted on an outer surface or an inner surface of the sterile bag or on the medical component packed in the sterile bag.

7. The method according to claim 1, wherein a plurality of medical components are packed in the sterile bag, and further comprising collectively comparing pieces of the component information regarding the plurality of medical components with the verifying unit and collectively verifying whether the medical components are appropriate for being attached to the apparatus body.

8. The method according to claim 1, wherein the apparatus body is a plurality of apparatus bodies, the method further comprising:
connecting the plurality of the apparatus bodies to a central monitoring apparatus and
transmitting pieces of the treatment information regarding the blood purification treatment for the patient to the storage unit of one of the respective plurality of apparatus bodies.

9. The method according to Claim 1, wherein the medical component is configured to be attached to the attaching position of the apparatus body, the medical component is configured to provide the blood purification treatment to the patient.

* * * * *